US00RE34405E

United States Patent [19]

Gould et al.

[11] E Patent Number: Re. 34,405

[45] Reissued Date of Patent: Oct. 12, 1993

[54] DETERMINATION OF ANALYTES IN PARTICLE-CONTAINING MEDIUM

[75] Inventors: Dennis R. Gould, San Gregorio; Robert F. Zuk, Burlingame, both of Calif.

[73] Assignee: Abbott Laboratories, Abbott Park, Ill.

[21] Appl. No.: 120,455

[22] Filed: Nov. 12, 1987

Related U.S. Patent Documents

Reissue of:

[64] Patent No.: 4,552,839
Issued: Nov. 12, 1985
Appl. No.: 519,300
Filed: Aug. 1, 1983

[51] Int. Cl.[5] ..... G01N 33/535; G01N 33/536; G01N 33/538; G01N 33/52

[52] U.S. Cl. ..... 435/7.1; 435/7.2; 435/7.22; 435/7.31; 435/7.32; 435/7.9; 435/805; 435/810; 435/975; 436/536; 436/541; 436/810; 436/824; 422/56

[58] Field of Search ..... 422/56; 435/7, 805, 435/810, 7.1, 7.2, 7.2, 7.31, 7.32, 7.9, 975; 436/536, 541, 810, 824

[56] References Cited

U.S. PATENT DOCUMENTS

| | | | |
|---|---|---|---|
| 3,378,481 | 4/1968 | Saravis et al. | 204/299 R |
| 3,389,966 | 6/1968 | Saravis | 436/515 |
| 3,482,943 | 12/1969 | Csizmas et al. | 422/56 |
| 3,552,925 | 1/1971 | Fetter | 436/169 |
| 3,645,687 | 2/1972 | Nerenberg | 436/514 |
| 3,825,410 | 7/1974 | Bagshawe | 436/514 |
| 3,888,629 | 6/1975 | Bagshawe | 436/541 |
| 3,915,647 | 10/1975 | Wright | 435/299 |
| 3,928,139 | 12/1975 | Dorn | 435/34 |
| 3,990,852 | 11/1976 | Piazzi et al. | 422/102 |
| 4,059,405 | 11/1977 | Sodickson et al. | 436/44 |
| 4,098,876 | 7/1978 | Piasio et al. | 436/500 |
| 4,111,754 | 9/1978 | Park | 435/310 |
| 4,116,844 | 9/1978 | Hein et al. | 210/446 |
| 4,168,146 | 9/1979 | Grabb et al. | 435/7.92 |
| 4,201,763 | 5/1980 | Monthony et al. | 436/533 |
| 4,205,058 | 5/1980 | Wagner et al. | 436/500 |
| 4,222,744 | 9/1980 | McConnell | 436/514 |
| 4,225,669 | 9/1980 | Meinick et al. | 435/29 |
| 4,233,402 | 11/1980 | Maggio et al. | 435/5 |
| 4,244,940 | 1/1981 | Jeong et al. | 436/500 |
| 4,246,339 | 1/1981 | Cole et al. | 435/5 |
| 4,264,766 | 4/1981 | Fischer | 536/51 |
| 4,270,920 | 6/1981 | Kondo et al. | 436/170 |
| 4,283,490 | 8/1981 | Plakas | 435/8 |
| 4,287,300 | 9/1981 | Gibbons et al. | 435/5 |
| 4,299,916 | 11/1981 | Litman et al. | 435/6 |
| 4,301,139 | 11/1981 | Feingers et al. | 436/500 |
| 4,307,188 | 12/1981 | White | 435/4 |
| 4,317,726 | 3/1982 | Shepel | 210/236 |
| 4,336,337 | 6/1982 | Wallis et al. | 435/292 |
| 4,342,739 | 8/1982 | Kakimi et al. | 424/1.1 |
| 4,366,241 | 12/1982 | Tom et al. | 435/7.91 |
| 4,376,110 | 3/1983 | David et al. | 436/513 |
| 4,378,428 | 3/1983 | Farina et al. | 435/7.23 |
| 4,391,904 | 7/1983 | Litman et al. | 435/7.91 |
| 4,407,943 | 10/1983 | Cole et al. | 435/7.22 |
| 4,425,438 | 1/1984 | Bauman et al. | 436/530 |
| 4,431,307 | 2/1984 | Suovaniemi | 356/246 |
| 4,435,504 | 3/1984 | Zuk et al. | 435/7.91 |
| 4,446,233 | 5/1984 | Auditore-Hargreaves et al. | 435/5 |
| 4,447,526 | 5/1984 | Rupchock et al. | 435/7.7 |
| 4,447,527 | 5/1984 | Monte et al. | 435/7.9 |
| 4,456,689 | 6/1984 | Witty et al. | 436/500 |
| 4,459,358 | 7/1984 | Berke | 436/170 |
| 4,459,361 | 7/1984 | Gefter | 436/523 |
| 4,461,829 | 7/1984 | Greenquist | 435/7.72 |
| 4,468,271 | 8/1984 | Pierson | 156/220 |
| 4,472,498 | 9/1984 | Masuda et al. | 435/7.7 |
| 4,476,231 | 10/1984 | Deindoerfer et al. | 436/534 |
| 4,477,575 | 10/1984 | Vogel et al. | 436/170 |
| 4,506,019 | 3/1985 | Lee | 436/500 |
| 4,517,288 | 5/1985 | Giegel et al. | 435/5 |
| 4,521,521 | 6/1985 | Abbott et al. | 436/517 |
| 4,533,629 | 8/1985 | Litman et al. | 435/7.91 |
| 4,543,338 | 9/1985 | Chen | 436/170 |
| 4,549,655 | 10/1985 | Forsythe, Jr. et al. | 206/569 |
| 4,562,148 | 12/1985 | Sommer | 435/7.72 |
| 4,594,327 | 6/1986 | Zuk et al. | 436/514 |
| 4,624,929 | 11/1986 | Ullman | 436/179 |
| 4,652,533 | 3/1987 | Jolley | 435/5 |
| 4,666,863 | 5/1987 | Edwards et al. | 436/514 |

FOREIGN PATENT DOCUMENTS

| | | |
|---|---|---|
| 0141547A1 | of 0000 | European Pat. Off. . |
| 0021214A1 | 1/1981 | European Pat. Off. . |

2421035 11/1974 Fed. Rep. of Germany ..... 436/541

OTHER PUBLICATIONS

Derwent Abstract 59604C/34 Asahi Chemical Ind KK J5 5090-858.

Derwent Abstract 57601A/32 Eisai KK J5 3075-322.

Derwent Abstract 88490B/49 Mitsubishi Chem Ind KK (Teik) J5 4139-595.

Abstract 58-755(A) Olympus Kogaku Kogyo K.K. "Vessel for Decision of Particle Cohesion and Decision Apparatus of Particle Cohesion Using This Vessel".

Abstract 58-223758(A) Olympus Kogaku Kogyo K.K. "Immunoassay Method and Reaction Vessel Used for Same Method".

Derwent Abstract 04835 J/49 Knapp "Capillary tube for radio immunoassay investigations-has fine filter and suction nozzle at end".

N. G. Anderson, Analytical Biochemistry, vol. 38, 1970, pp. 175-189.

*Primary Examiner*—Christine M. Nucker
*Assistant Examiner*—Kay Kim
*Attorney, Agent, or Firm*—Richard D. Schmidt

[57] ABSTRACT

Methods and compositions are provided for concentrating particles in a minute area on a solid surface. The method permits the detection of small amounts of analytes by providing for an observable signal in relation to the concentration of particles in the area.

46 Claims, 1 Drawing Sheet

DETERMINATION OF ANALYTES IN PARTICLE-CONTAINING MEDIUM

Matter enclosed in heavy brackets [ ] appears in the original patent but forms no part of this reissue specification; matter printed in italics indicates the additions made by reissue.

BACKGROUND OF THE INVENTION

The clinical laboratory has become an increasingly important adjunct to medicine, both in diagnosis and therapy. As the variety of situations in which determinations are desired have expanded, there has been an increasing variety of approaches for measuring the substance of interest. There are many considerations involved in the development of the assay. One consideration is the simplicity of the protocol. The more measurements and steps that are required, the greater the likelihood for error. A second consideration is the concentration range and absolute amount to be measured. A third consideration is the nature of the sample involved. A fourth consideration is the nature of pretreatments which may be required. A fifth consideration is the nature of interfering substances in the samples. A sixth consideration is the intended environment in which the assay is performed and the technical skill of the persons who will perform the assay. This will also involve whether an instrument is to be used or only a visual determination. Thus, each new development provides advantages which find particular applications as to analytes, preparation of reagents, nature of the users, and manner of performance.

DESCRIPTION OF THE PRIOR ART

Anderson, Anal. Biochem. (1970) 38:175–189 describes the use of cellulose wicks to monitor agglutination reactions.

SUMMARY OF THE INVENTION

Novel methods and compositions are provided for determining the presence of analytes in a particle containing medium, where the analyte of interest may be bound or unbound to the particle in a sample. By contacting the assay medium with a bibulous material at a liquid air interface, a small situs, usually a thin band or concentrated point, of particles can be obtained adjacent the interface, which site provides a signal which can be related to the presence of analyte in the sample. The particles include synthetic particles, cells, and immune complex aggregates. The size and nature of the particles, as well as the nature of the aqueous medium, can be used to modulate the formation of the small site.

DESCRIPTION OF THE SPECIFIC EMBODIMENTS

The subject invention is based on the concentration of particles at a small site, generally having one dimension less than about one mm wide, on a bibulous solid support in relation to the presence or absence of an analyte in a sample. The site may be a point, a straight or curved band, or the like. The concentration of particles at the predetermined site can be used to provide a detectable signal at a site. The sample may influence the concentration of the particles at the site and/or the production of a detectable signal. The detectable signal will be determined in a detection zone, which may or may not be the concentration site.

The particles which are involved in the assay may be present in the sample, may be added as reagents or formed in situ. The nature of the particle may vary widely, being naturally occurring or synthetic, being a single material, a few materials, or a combination of a wide variety of materials. Naturally occurring particles include nuclei, mycoplasma, plastids, mammalian cells, unicellular microorganisms, e.g., bacteria, etc. Synthetic particles may be prepared from synthetic or naturally occurring materials, such as metal colloids or latex particles made from polystyrene polyacrylates or naturally occurring materials, such as polysaccharides, e.g., agarose, or the like. Non-naturally occurring particles may be varied depending upon the particular assay, the protocol for the assay, or other considerations.

The size of the particles will vary widely, generally ranging from about 0.05 to 100 microns, more usually from about 0.1 to 75 microns. The particles may be charged, either positively or negatively, may be amphoteric or lack any charge, being neutral. The presence or absence of charge will affect other parameters involved in the assay.

The means for detecting the detectable signal at or away from the concentration site may or may not be an intrinsic property of the particles. The particles may be labeled with a wide variety of materials which allow for detection, such as radionuclides, dyes, fluorescers, enzymes, or other convenient label providing for a detectable signal, either visually observable or detectable by instrumentation. The various labels would normally be covalently bonded to the particle, using linking arms as appropriate. The labels may be bound to the surface or, when feasible, extend throughout the particle.

Figure 1:
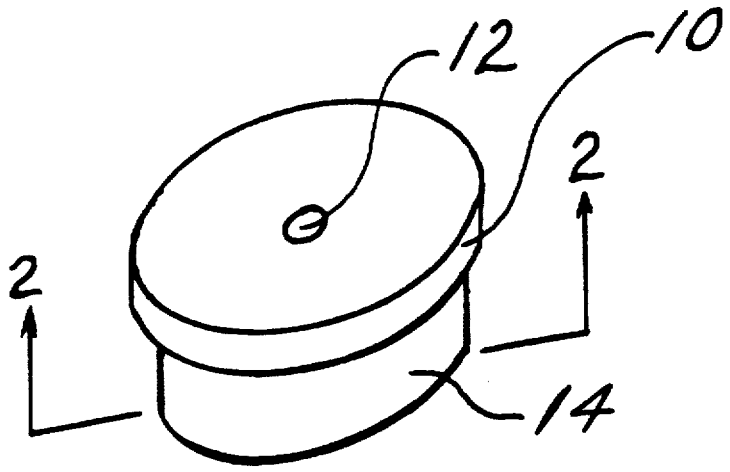
*FIG. 1 is a partial elevational view of a device in accordance with the present invention.*
Figure 2:
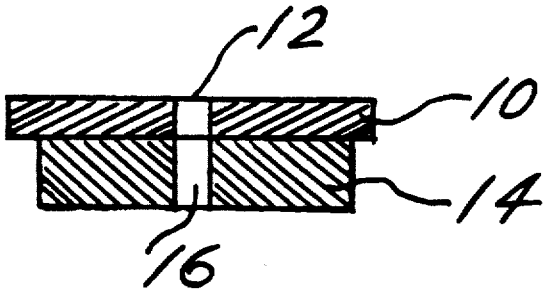
*FIG. 2 is a cross-sectional view of the device of FIG. 1.*

Any convenient bibulous absorbent solid material may be employed which allows for capillary transport of a liquid away from the interface between the air and liquid. Various materials include paper, cellulose particles, silica gel, cellulosic beads, glass fiber, filter paper, and the like. The surface should be relatively smooth, so as to allow for the formation of a concentrated particle site, for example, in the form of a sharp band or point. The size and shape of the bibulous material may be varied widely considering the purpose of the material. Namely, one wishes to form a fine band, curve, circle, line, or point by concentrating small particles which are relatively uniformly dispersed in a liquid medium. The concentrating is best achieved by transporting a relatively large volume through a relatively narrow area. The bibulous material may be shaped, therefore, as a narrow strip of from about one to about five millimeters in width, a triangular shaped structure having a rounded tip or a circular disc having a central small orifice or other structure. The size of the orifice may vary depending on whether the orifice extends solely through a non-bibulous support (*such as, for example, depicted in FIGS. 1 and 2 wherein non-bibulous member 10 has an orifice 12*), leaving the bibulous member underneath the orifice intact, or the orifice extends through the bibulous member underneath (*such as, for example, depicted in FIGS. 1 and 2 wherein bibulous member 14 has orifice 16*). In the first situation, the orifice will generally be about 0.10 to 2 mm, usually 0.25 to 1 mm. In the second case, the orifice will generally be less than one millimeter, ranging from about 0.1 to 0.5 mm. In each case, the bibulous material will usually have a support which provides structural strength. The non-bibulous material may be a water impermeable layer or coating.

The liquid medium will normally be an aqueous medium, which may have from about 0–40 volume percent of a miscible solvent such as alkanols, ethers, sulfoxides, amides, etc., generally ranging from about 1 to 6 carbon atoms.

In performing the subject invention, one usually wishes to concentrate or collect particles at the air-liquid interface depending upon the presence or absence of a predetermined condition. The condition will be the presence in the sample, above a predetermined amount, of an analyte which is a member of a specific binding pair.

By appropriate choice of conditions in the aqueous medium, one can modulate the size of particles which will concentrate at the air-liquid interface as contrasted with following the solvent front, so that no or few particles collect at the air-liquid interface, resulting in the absence of an observable site.

The choice of conditions will vary, with the nature of the particle, as to size, charge, polarity or other property which affects the repulsion or attraction of the particles to each other. In order to form the concentrated particle site, one wishes to distinguish between particles of a particular size or between different sized particles. In the former situation, the method serves to concentrate particles present in the medium above a predetermined size. In this situation, the particles do not undergo a change in size distribution as a result of the presence of an analyte. In the latter situation, the presence of an analyte will result in the binding together of particles, where the original sized particles would follow the solvent front, while particles which are bound together will remain on the bibulous surface at the air-liquid interface. Therefore, the conditions will be chosen so that particles of above a certain size will be retained at the air-liquid interface, while particles smaller than that size will travel away from the air-liquid interface.

Factors that affect the size of the particle which will migrate involve repulsive and attractive forces, which can be influenced by pH and ionic strength. Where the particles are heavily charged with the same charge, at a relatively high ionic strength, the charge will be neutralized which will allow the particles to aggregate or band together. Where the particles have acidic or basic groups, a pH can be chosen, to reduce the number of charges present on the particle. Conditions can be chosen so that the particles will not aggregate unless a binding means is provided. The binding means will be a member of a specific binding pair, which is polyvalent and is, therefore, capable of binding to at least two particles.

The pH will vary with the nature of the particle. For basic particles, one may induce repulsive charges by lowering the pH, while for acidic particles, one may induce repulsive charges by raising the pH. The pH will be chosen so as to maintain mild repulsion between particles, so as to encourage the transport of the particles, except where a plurality of particles are joined together.

Ionic strength may also be used in a similar fashion to modulate repulsion. By reducing or raising the ionic strength, one may modulate the repulsive effect between particles, so that at low ionic strength, one enhances the repulsive effect, while at high ionic strength, one reduces the repulsive effect between charged particles. Therefore, depending on the nature of the particles, one will modify the conditions of the medium. The various conditions will be optimized depending on the nature of the system.

The pH which is employed will generally be in the range of about 2 to 12, with the range varying from about 3 to 7 for positively charged particles and from about 6 to 11 for negatively charged particles. The ionic strength will generally vary from about $10^{-1}$ to $10^{-4}$. One may optimize these two parameters empirically depending upon the size and nature of the particles involved.

A further factor is the inclusion of surfactants in the assay medium. The surfactants aid in the migration of the particles through the bibulous support. By modifying the surface tension, migration of the particles may be enhanced or diminished. The surfactants may be anionic, cationic or non-ionic, preferably non-ionic or combinations of non-ionic and anionic. Surfactants will be used in minor amount, generally being present in from about 0 to 2 vol % of the assay medium, more usually from about 0.005–1.5 vol %, and preferably from about 0.01 to about 1 vol %. Various surfactants may be used, such as Tween 20, QS44, PEG 1500, etc.

Other factors may also be employed to affect properties of the assay medium. Chaotropic or antichaotropic agents may be employed. Illustrative chaotropic agents include fluoride ion and polyethylene glycol. Illustrative antichaotropic agents include trichloroacetate, thiocyanate and dextran. Agents to modify the viscosity of the medium may be employed. Elevated or reduced temperatures may also find application.

Method

As indicated previously, the subject method is predicated on either concentrating particles over a predetermined size at a localized site or being able to distinguish two sets of particles: (a) Particles which migrate with the solvent away from the air-liquid interface and (b) particles which form a localized site at the air-liquid interface. The latter situation will be the more common one.

In the former case, the primary function is concentrating particles which are present in a dilute solution. This situation may be exemplified by a mixture of particles where only a small percentage may be the particles of interest. For example, a clinical sample which has a heterogeneous population of cells, where one wishes to determine the presence of a particular species or strain. By employing a labeled antibody in the medium, one could rapidly tag any cells of interest. The presence of the tag at the localized site would be diagnostic of the presence of the particular cells. Any unbound label would follow the solvent front, minimizing any background. The absence of an observable band would indicate the absence of the cells of interest in the sample.

A particle is employed which migrates under the conditions of the assay, but in the presence of analyte in the medium, can be inhibited from migrating or permitted to migrate. In this way, one can relate the presence of a detectable signal at a localized site on a bibulous surface to the presence of the analyte of interest in the assay medium.

The concentration of particles at the localized site is achieved by providing bridges between particles of specific binding members. Specific binding members can be broken up into two primary groups: (1) ligands and receptors; and (2) complementary polynucleotides. The ligands and receptors involve organic molecules, where the ligand is any molecule for which a receptor is available or can be made. The ligand is characterized by having a polar and spatial organization which binds to a reciprocal or homologous receptor. The receptor is conventionally a macromolecule which has a structural organization complementary to the ligand so as to have a high avidity for the particular structure of the ligand to provide for a specific binding complex. Conventional receptors include antibodies and fragments thereof, enzymes, naturally occurring receptors, and the like.

In the subject invention, the ligands may be haptens or antigens, but where the ligand is monovalent and has to serve as a bridge, it will be provided in a polyvalent form. The polynucleotides may be DNA or RNA, where the bridge will have a sufficiently extended complementary sequence, for example, by repeating the same sequence to allow binding to two different fragments of complementary polynucleotide sequences.

In carrying out the method, one combines the sample, the assay medium having the appropriate conditions for the particles, particles, if particles are to be added, and the bridging system for bridging the particles. Depending upon the manner in which the localized site is to be detected, a signal producing system may also be involved, where one or more labels are provided bound to members of the bridging system or to binding members which bind to the analyte. By having two different binding members involved in the production of a detectable signal, one can provide for detection of an analyte having two different reciprocal binding members.

After combining the sample with the bridging members and any signal producing members, as appropriate, in an appropriate assay medium, one then contacts a small portion of the bibulous member with the assay medium, where a major portion of the bibulous member does not contact the assay medium and may act as a wick or well for absorbing liquid, for example, by capillary or wicking action, so as to draw liquid through the area at the air-liquid interface.

After sufficient time to allow for a sufficient proportion of the assay medium to be absorbed by the bibulous member, so that concentrations of the particles at the localized site can form, as appropriate, contact with the assay medium may be terminated. Depending upon the signal producing system, the presence of the site may be determined or additional members of the signal producing system may be added to the area at which the site may have formed to provide a detectable signal. If a quantitative result is desired, the detectable signal may be measured by any convenient means.

To further illustrate the subject invention, the following illustrative examples will be described. In an assay for a hapten, one could provide colored beads to which a hapten is covalently bonded by an appropriate linking arm. The assay conditions and size of beads, as well as the nature of the bibulous member, would be chosen, so that the individual beads would migrate with the solvent, and no band would be observed. One could then combine the sample and antibodies, so that at a concentration of interest of the analyte, a major proportion of the antibody sites would be filled by the available hapten.

After sufficient time for binding to occur, one could then add the particles to the assay medium and incubate a second time to allow for binding of any available antibody binding sites to the hapten on the colored beads. In the absence of hapten in the sample, there would be a substantial amount of bridging between the beads by the antibodies.

One would then contact the bibulous member with the assay medium and allow a sufficient amount of the assay medium to be wicked into the bibulous member so that a substantial number of particles may traverse the air-liquid interface adjoining the bibulous member. Based on the color of the beads, one would observe a sharp, distinct band in the absence of hapten and substantially no beads in the presence of hapten. Where one is interested in a range of concentration of the hapten, a controlled amount of the assay medium would be absorbed by the wick and the concentration of particles determined by appropriate spectrophotometric measurements, e.g., using a reflectometer. This result could be compared with the result observed with a sample having a known amount of the hapten.

A second illustrative example is the determination of an antigen. Beads could be provided which are labeled with antibodies to the antigen and an enzyme, for example, horseradish peroxidase. One would combine the beads under conditions where individual beads would migrate with the solvent, but linked beads would remain at the juncture of the air-liquid interface. One would combine the beads with the sample and incubate the mixture for sufficient time to allow the antigen to bind to the antibodies to provide bridges between the beads. One would then introduce the bibulous member as before and allow a sufficient amount of the liquid medium to be wicked by the bibulous member.

After a sufficient amount of the medium had been wicked through the bibulous member to allow for the formation of a narrow band or point, the bibulous member would be removed from the assay medium and placed in a development solution containing hydrogen peroxide and a substrate for horseradish peroxidase, which upon oxidation forms a color, desirably forms an insoluble dye, which precipitates onto the beads. In this manner, the band or point would become visually observable where particles are present to which horseradish peroxidase has become bound or retained.

A third illustrative example is where one is interested in a particular bacterial strain. In this method one might choose a bibulous member circle mounted on a non-bibulous plastic support having a centrally located orifice of about 0.5 mm dia. A swab is taken of a clinical sample and dispersed in PBS-0.05% Tween 20. To the dispersion is added a monoclonal antibody conjugated to an enzyme and the mixture is incubated. A few drops of the sample are placed over a device comprising a lower bibulous disc bonded to an upper hydrophobic plastic disc having a central orifice of about 0.5 mm dia. The liquid passes through the orifice and spreads evenly outward from the orifice with the organisms concentrated to the spot on the bibulous member underneath the orifice. The monoclonal antibody-enzyme conjugate will bind to any organisms which have the reciprocal epitopic site. Excess monoclonal antibody-enzyme will wick away so that only specifically bound enzyme will remain as the spot. To ensure removal of residual enzyme which is not specifically bound, a few drops of the PBS-Tween 20 solution may be placed over the orifice and allowed to wick. About 0.05 ml of a developer solution is then added, e.g., $H_2O_2$+4-chloronaphthol with HRP as the enzyme and the solution allowed to wick. Color will indicate the presence of the organism.

A large number of patents have been issued which describe a wide variety of labels which have found use in diagnostic assays. Various protocols can be developed where these labels may be used with advantage. Illustrative of such patents are U.S. Pat. Nos. 3,850,752; 4,255,329; 4,233,402; and 4,208,479.

For performing the method, kits can be provided where the various reagents are combined in predetermined amounts in combination with various ancillary materials for combination with the sample. In view of the wide spectrum of protocols and reagents, a wide variety of kits may be prepared. For the most part, where the method involves the addition of particles, the kits will involve particles which have a member of a specific binding pair substantially irreversibly bound to the particle, either covalently or non-covalently. Also, there may be a label bound to the surface of the particle or dispersed therein, particularly a dye, which may be colored in the visible range of fluorescent. In some instances, the particle may also be labelled with an enzyme.

Where particles are not to be included, the reagents will normally involve labelled receptors or ligands, where the labels provide for a detectable signal and may provide for the inhibition of migration of the particles present in the assay medium. In addition to the labelled reagents, there will be ancillary reagents such as buffers, stabilizers, detergents, and as appropriate substrates for enzymes, bulking agents, and the like. Also included in such kits would be the wicking material—prepared as strips or discs—with precut orifices, etc.

The following examples are offered by way of illustration and not by way of limitation.

EXPERIMENTAL

In the following experiment, a variety of beads of different colors and sizes were combined to demonstrate that one could achieve bands of different colors depending upon the sizes of the beads and their color and the effect of the combination of the beads in a band. The protocol was to combine 0.05 ml of each 2% bead preparation plus 20 ml of a 1% solution of normal sheep serum in PBS containing 0.05% QS44 and 0.05% Tween 20. The paper which was employed was triangular-shaped Millipore membrane paper with a rounded tip, where the tip was inserted into the assay medium. This shape provides for enhanced concentration of the particles, while providing a large wicking reservoir.

The following table indicates the beads that were employed, the expected color and the observed color.

TABLE 1

| | Bead Color | | | Color | |
|---|---|---|---|---|---|
| | Red | Blue | Yellow | | |
| | | Size, μ | | Expected | Observed |
| 1. | .15 | .5 | .5 | green | green |
| 2. | .5 | .25 | .5 | orange | orange |
| 3. | .5 | .5 | .25 | purple | purple |
| 4. | .15 | .25 | .5 | yellow | yellow |
| 5. | .5 | .25 | .25 | red | red |
| 6. | .15 | .5 | .25 | blue | blue |
| 7. | .5 | .5 | .5 | brown | brown |

TABLE 1-continued

| | Bead Color | | | Color | |
|---|---|---|---|---|---|
| | Red | Blue | Yellow | | |
| | | Size, μ | | Expected | Observed |
| 8. | .15 | .25 | .25 | white | No color |

The colors were predicted based on the 0.5 micron particles being retained on the surface adjacent the interface, while the small particle migrated with the solvent front; thus, the complementary color of the larger beads is seen.

In the next experiment, an assay was performed to detect the presence of Streptococcus pyogenes (Lancefield Group A) in a mixture of Group A and Group B. The assay medium was prepared by removing cells of the two organisms from agar growth by loop and suspending them in 1 ml of PBS plus 0.05% Tween 20. A mouse monoclonal antibody against Group A (anti-A) at about 5 mg/ml was employed. Also employed was goat antibodies against mouse IgG (G-anti-IgG) which was conjugated to horseradish peroxidase. As a developing solution, a solution was employed containing 200 μg/ml of sodium 4-chloro-2-naphthol, 50 mM glucose, 2 mg/ml bovine serum albumin and excess hydrogen peroxide. The protocol was to combine 100 ml of the organism solution (about $10^7$ cells/ml), 20 μl of the antibody-horseradish peroxidase conjugate and 20 μl of the anti-A, incubate the mixture and then wick 50 ml on a cellulose strip (cellulose strips used for tlc). The strip was then placed in the substrate solution and a dark band formed indicating the presence of Group A organisms.

A similar experiment was carried out, where enzyme channeling was involved, demonstrating a rapid antibiotic sensitivity assay.

Group A strep. pyogenes (0.2 ml of $10^8$ cells/ml) were incubated for 2¾ hrs. at 37° C. in the presence or absence of penicillin at 2 units/ml. This solution was then combined with 0.8 ml of phosphate buffered saline (0.02 ml phosphate plus 0.05% Tween 20 - pH 7.2) followed by the addition of 0.01 ml of a monoclonal anti-Group A antibody conjugated to horseradish peroxidase (HRP). 0.2 ml of this mixture was wicked for 7 min. with a cellulose TLC paper strip. The wick was then transferred into developer (0.2 ml of the above-described 4-chloronaphthyl substrate solution plus 0.5 μl glucose oxidase). The wick was developed for 30 min.

RESULTS

Bacterial cells exposed to the penicillin formed a less intense blue-purple band than did the unexposed cells. The difference was easily detectable by the eye.

It is evident from the above results, that a simple rapid method is provided for detecting the presence of an analyte. The method can be qualitative or quantitative and can be used with a variety of protocols which can be adapted to particular samples. Furthermore, simple equipment is employed and the results can be obtained by visual observation.

Although the foregoing invention has been described in some detail by way of illustration and example for purposes of clarity of understanding, it will be obvious that certain changes and modifications may be practiced within the scope of the appended claims.

What is claimed is:

1. A method for detecting the presence of a member of a specific binding pair ("sbp member") in a [liquid assay medium] *sample*, said specific binding pair consisting of ligand and homologous receptor, where said method involves particles to which are bound at least one member of a specific binding pair, a solid bibulous member and a signal-producing system which involves at least one label which is bound to said particles or an sbp member, said method comprising:

combining in an aqueous assay medium, [said] a sample *suspected of containing an sbp* member and at least one *of the group consisting* of said particles and *said* labeled sbp members, with the proviso that particles are added when said sample lacks particles having an sbp member; under conditions where particles only within a predetermined size[,] range and charge will concentrate in an area on said bibulous member adjacent the air/liquid interface, when said bibulous member is contacted with said assay medium;

contacting said bibulous member with said assay medium whereby said assay medium is wicked past said area and particles within said predetermined size *range* and charge concentrate at a small site in said area; and detecting the signal as a result of said signal-producing system, wherein said signal is related to the amount of label in said area and the amount of label in said area is related to the amount of said sbp member in said sample.

2. A method according to claim 1, wherein said sample has particles within said predetermined size *range* to which are bound an sbp member.

3. A method according to claim 1, wherein said sample has particles below said predetermined size *range* to which are bound an sbp member and said label is joined to a polyvalent homologous sbp member.

4. A method according to claim 1 wherein said particles are labeled with a member of said signal producing system.

5. A method for detecting cells that have at least one predetermined determinant site, where said method involves labeled receptors which bind to said determinant site or to receptors binding to said determinant site, and a solid bibulous member, where the label of said labeled receptor by itself or in combination with other members of a signal producing system produces a detectable signal, said method comprising:

combining in an aqueous assay medium, a sample suspected of containing said cells, labeled receptors to said determinant site or receptors for said determinant site and labeled receptors for said receptors, under conditions where individual cells migrate along a bibulous member away from an air-liquid interface when said medium is contacted with said bibulous member, but receptor linked cells concentrate at [the] *an* area of *said* bibulous member at the air-liquid interface;

contacting said bibulous member with said assay medium, whereby linked cells concentrate in said area; and detecting the signal as a result of said signal producing system wherein said signal is related to the amount of label in said area.

6. A method according to claim 5, wherein said cell is a bacterial cell, fungal *cell*, protozoan *cell*, or other parasitic or infectious agent.

7. A method according to claim 5, wherein said label is an enzyme.

8. A method according to claim 5, wherein said bibulous member has a small orifice surrounded [on one side of said bibulous member] with a water impermeable layer and said assay medium is contacted with said bibulous member at said orifice.

9. A method according to claim 5, wherein said bibulous member is supported by a plastic support having a centrally located orifice.

*10. A method according to claim 1 wherein after said contacting of said bibulous member with said assay medium, said area on said bibulous member is contacted with an aqueous medium containing a labeled sbp member when said labelled sbp member is not included in said assay medium.*

*11. A method according to claim 1 wherein said contacting is carried out by introducing a portion of said bibulous member into said assay medium.*

*12. A method according to claim 1 wherein said contacting is carried out by introducing a portion of said assay medium onto said bibulous member.*

*13. A method according to claim 1 wherein said combining is carried out by combining said sample in an aqueous medium with said particles and said contacting is carried out by contacting said assay medium with a portion of said bibulous member.*

*14. A method for detecting the presence of an analyte, said method comprising:*

*combining a medium suspected of containing said analyte, which is a member of a specific binding pair (sbp), with particles having bound thereto an sbp member reciprocal to said analyte,*

*contacting said medium with an area of a bibulous member under conditions where said medium wicks away from said area and at least a portion of said particles concentrate in a localized site on said bibulous member, and*

*examining said site to determine the presence of said analyte.*

*15. The method of claim 14 wherein said particles have a label.*

*16. The method of claim 14 wherein said examining is carried out by (1) contacting said site with a medium containing a labeled receptor for said analyte and (2) determining the presence of said labeled receptor at said site to determine the presence of said analyte.*

*17. The method of claim 14 wherein said examining is carried out by (1) contacting said site with a medium containing a labeled receptor for said reciprocal sbp member and (2) determining the presence of said labeled receptor at said site to determine the presence of said analyte.*

*18. The method of claim 14 wherein said site is examined by contacting said site with members of a signal producing system and then examining said site for the presence of a detectable signal to determine said analyte.*

*19. The method of claim 14 wherein said medium wicks away from said area by migrating outward along said bibulous member.*

*20. A method for detecting the presence of an epitopic site on particles, said method comprising:*

*contacting a spot on a bibulous member with a medium containing a labelled antibody reciprocal to said epitopic site and particles suspected of having said epitopic site under conditions where excess of said labelled antibody will wick away from said spot; and*

*detecting the presence of said labelled antibody at said spot.*

*21. The method of claim 20 wherein said antibody is labelled with an enzyme or a fluorescer.*

*22. A method for detecting the presence of an analyte, said method comprising:*

*providing in combination an aqueous medium suspected of containing said analyte, which is a member of a specific binding pair (sbp), particles having bound thereto an sbp member reciprocal to said analyte, and an area of a bibulous member under conditions where said medium wicks away from said area and at least a portion of said particles concentrate in a localized site on said bibulous member, and*

*examining said site to determine the presence of said analyte.*

*23. The method of claim 22 wherein said particles have a label.*

*24. The method of claim 22 wherein said examining is carried out by (1) contacting said site with a medium containing a labeled receptor for said analyte and (2) determining the presence of said labeled receptor at said site to determine the presence of said analyte.*

*25. The method of claim 22 wherein said examining is carried out by (1) contacting said site with a medium containing a labeled receptor for said reciprocal sbp member and (2) determining the presence of said labeled receptor at said site to determine the presence of said analyte.*

*26. The method of claim 22 wherein said examining is carried out by (1) contacting said site with members of a signal producing system and then (2) determining the presence of a detectable signal at said site to determine the presence of said analyte.*

*27. The method of claim 22 wherein said medium wicks away from said area by migrating outward along said bibulous member.*

*28. A device for conducting an assay, said device comprising a non-bibulous member having an orifice and serving as a support for a bibulous member, said bibulous member having an orifice that extends through said bibulous member, said orifices corresponding in location.*

*29. The device of claim 28 wherein said orifice of said bibulous member and said orifice of said support are centrally located.*

*30. The device of claim 28 wherein said bibulous member is a circular disc.*

*31. A kit comprising in packaged form:*

*a device comprising a non-bibulous member having an orifice and serving as a support for a bibulous member such that, when said device is used in conducting an assay, liquid containing particles applied to said bibulous member through said orifice migrates away from point of application and at least a portion of the particles present in said liquid concentrate at said joint of application and in a separate container particles which have bound irreversibly thereto a member of a specific binding pair.*

*32. The kit of claim 31 which further comprises in a separate container a member of a signal producing system.*

*33. A method for detecting the presence of a member of a specific binding pair ("sbp member") in a sample, said specific binding pair consisting of ligand and homologous receptor, where said method involves particles to which are bound at least one member of a specific binding pair, a solid bibulous member and a signal-producing system which involves at least one label which is bound to an sbp member,*

*said method comprising:*

*combining in an aqueous assay medium, a sample suspected of containing an sbp member and said particles and said labeled sbp member under conditions where said particles concentrate in an area on said bibulous member adjacent the air/liquid interface, when said bibulous member is contacted with said assay medium;*

*contacting said bibulous member with said assay medium whereby said assay medium is wicked past said area and particles concentrate at a small site in said area; and*

*detecting the signal as a result of said signal-producing system, wherein said signal is related to the amount of label in said area and the amount of label in said area is related to the amount of said sbp member in said sample.*

*34. The method of claim 33 wherein said label is an enzyme.*

*35. The method of claim 33 wherein said sbp member in said sample is an antigen, said sbp member bound to said particles is an antibody for said antigen and said sbp member bound to said label is an antibody.*

*36. The method of claim 33 wherein said sbp member in said sample is a hapten, said sbp member bound to the particles is an antibody for said hapten and said sbp member bound to said label is said hapten.*

*37. A method for detecting the presence of an analyte, said method comprising:*

*combining a medium suspected of containing said analyte, which is a member of a specific binding pair (sbp), with particles having bound thereto an sbp member reciprocal to said analyte and with a labeled sbp member wherein the amount of labeled sbp member which binds to said particles is related to the amount of analyte in said medium,*

*contacting said medium with an area of a bibulous member under conditions where said medium wicks away from said area and said particles concentrate in a localized site on said bibulous member, and*

*examining said site for the presence of labeled sbp member to determine the presence of said analyte.*

*38. The method of claim 37 wherein said site is contacted with members of a signal producing system and then is examined for the presence of a detectible signal to determine the analyte.*

*39. The method of claim 37 wherein said medium wicks away from said area by migrating outward along said bibulous member.*

*40. A method for performing an immunoassay for an analyte in a sample, which method comprises providing a chromatographic medium, forming a reaction mixture containing a specific binder for the analyte, said specific binder being immobilized by attachment to a particulate solid phase, and a labeled reagent partly in a form which is mobile on said medium and partly in the form of a labeled analyte/specific binder reaction product insolubilized so as to be immobile on the medium, the proportions of the two forms being determined by the amount of analyte in the sample, applying the reaction mixture to a spot on the chromatographic medium, causing the mobile form of the labeled reagent to migrate from the spot, and thereafter, observing one or both of the mobile and immobile, insolubilized forms of the labeled reagent.*

*41. The method as claimed in claim 40, wherein the chromatographic medium is in sheet form, with the reaction mixture being applied to a spot on the sheet and the mobile form of the labeled reagent being caused to migrate radially from the spot.*

*42. The method as claimed in claim 40, wherein migration is assisted by subsequent application to the spot of a*

*solvent which causes mobile species, but not immobile species, to migrate through the chromatographic medium.*

*43. The method as claimed in claim 42, wherein the solvent is an aqueous liquid.*

*44. The method as claimed in claim 42 wherein the reaction mixture is formed by causing the analyte in the sample, and a labeled version of the analyte, to compete for reaction with a limited amount of a specific binder for the analyte, the analyte/specific binder complex being rendered insoluble.*

*45. The method as claimed in claim 44, wherein the analyte/specific binder complex is rendered insoluble by reaction of the specific binder with its antibody, said reaction being effected before, during and after incubation with the analyte.*

*46. The method as claimed in claim 40, wherein the reaction mixture is formed by causing the analyte in the sample to bind to an excess of an immobilized specific binder and a labeled specific binder for the analyte is caused to bind to vacant binding sites of the analyte.*

* * * * *